United States Patent [19]

Armand et al.

[11] Patent Number: 4,505,997
[45] Date of Patent: Mar. 19, 1985

[54] BIS PERHALOGENOACYL -OR SULFONYL-IMIDES OF ALKALI METALS, THEIR SOLID SOLUTIONS WITH PLASTIC MATERIALS AND THEIR USE TO THE CONSTITUTION OF CONDUCTOR ELEMENTS FOR ELECTROCHEMICAL GENERATORS

[75] Inventors: Michel B. Armand, Nancy, France; Fouzia El Kadiri Cherkaoui el Moursli, Sale, Morocco

[73] Assignees: Agence Nationale de Valorisation de la Recherche (ANVAR), Paris; Societe Nationale Elf Aquitaine, Courbevoie, both of France

[21] Appl. No.: 500,193

[22] Filed: Jun. 1, 1983

[30] Foreign Application Priority Data

Jun. 1, 1982 [FR] France ............................. 82 09540

[51] Int. Cl.$^3$ .................... H01M 6/18; H01G 4/14; C07C 119/06
[52] U.S. Cl. ................... 429/192; 252/62.2; 564/82; 564/159
[58] Field of Search ............ 429/192; 252/62.2; 564/82, 159

[56] References Cited

U.S. PATENT DOCUMENTS 4,281,072 7/1981 Wetton et al. ................... 252/62.2
4,303,748 12/1981 Armand et al. ................... 429/192

FOREIGN PATENT DOCUMENTS 2610853 9/1977 Fed. Rep. of Germany .

Primary Examiner—Donald L. Walton
Attorney, Agent, or Firm—Weiser & Stapler

[57] ABSTRACT

The invention relates to novel ionic compounds which can be incorporated in polymers whose monomer units include at least one hetroatom, particularly oxygen or nitrogen adapted to form bonds of the donor-acceptor type with the cation of the ionic compound, the solid solutions obtained being utilizable to form the electrolyte of an electrochemical generator. These ionic compounds are represented by the formula $(C_nX_{2n+1}Y)_2N^-, M^+$ in which : X is a halogen, n varies from 1 to 4, Y is a CO or $SO_2$ group and M is an alkali metal.

18 Claims, 2 Drawing Figures

BIS PERHALOGENOACYL -OR SULFONYL-IMIDES OF ALKALI METALS, THEIR SOLID SOLUTIONS WITH PLASTIC MATERIALS AND THEIR USE TO THE CONSTITUTION OF CONDUCTOR ELEMENTS FOR ELECTROCHEMICAL GENERATORS

The invention relates to a novel ionic compound having the formula $M^+X^-$, in which M is a cation derived from an alkali metal or ammonium ion, and $X^-$ is an anion having a behaviour similar to that of a strong acid. The invention relates more particularly to ionic compounds which can be dissolved within a macromolecular material formed at least in part of one or several homo and/or copolymers derived from one or several monomeric units including at least one hetereoatom, particularly oxygen or nitrogen, adapted to form bonds of the donor-acceptor type with the cation of the ionic compound. More particularly still, the invention relates to ionic compounds of this type, which can be dissolved in at least certain of plastic materials, such as those which have been described in European Patent Application No. 00 13199 entitled "Electrochemical generators for the production of current and novel materials for their manufacture."

The invention also relates to the solid solutions themselves, which have thus been obtained and which, like those more particularly described in the above-said European patent application, are endowed with a sufficient cationic conductivity to be useful for the production of solid electrolytes for the constitution of electrochemical generators, preferably rechargeable. These solid solutions are again useful for the constitution of electrochemical generator electrodes, when these electrodes are constituted by the product of agglomeration into a composite mass of the active material of the latter and, if necessary, of a compound inert to electronic conduction, on the one hand and of the above solid solution, on the other hand.

It is self-evident that the solid solutions according to the invention may resort to any other type of plastic material to the extent that their characteristics of reciprocal solubility are sufficient for obtaining a solid solution having a cationic conductivity of $10^{-5}$ ohms$^{-1}\times$cm$^{-1}$, preferably at at temperature not exceeding 130° C.

The ionic compounds according to the invention may be represented by the formula:

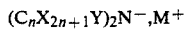

in which:
X is a halogen,
n varies from 1 to 4
Y is a CO or $SO_2$ group and
M is alkali metal.

The group X may be chlorine, bromine and iodine or, preferably, fluorine.

M is preferably constituted by lithium or sodium. It may be also constituted by potassium.

The compounds obtained are named: -bis-perhalogeno-acyl-imides, when Y is constituted by the CO group and -bis-perhalogeno-sulfonyl-imides, when the group Y is constituted by the $SO_2$ group.

The invention also relates to a process for the preparation of the above indicated compound.

Figure 1:
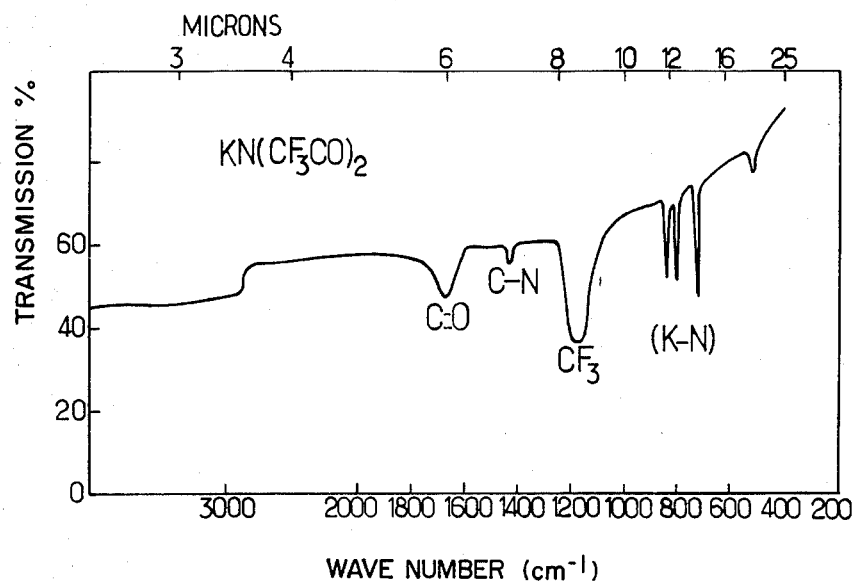
FIG. 1 is an IR spectrum of the compound potassium bis(trifluoromethyl acetyl) imide.

To form the compound according to the invention, and particularly the bis-perhalogeno-acylimides, recourse will advantageously be had to the reaction which consists of reacting the anhydride of the formula

in which X, n and Y have the above indicated meanings, with a cyanate of a heavier alkali metal, preferably potassium, the reaction being completed, in the case where it is desired to obtain a bis-perhalogeno-acylimide (or a bis-halogeno-sulfonyl-imidide) of lithium or of sodium, by a ionic exchange reaction in solution with a salt of lithium or sodium whose anion is adapted to form, with the potassium ions, a salt which is insoluble in the reaction medium, the ionic compound containing the lithium or sodium cation then being seperable from the reaction medium.

To form the bis-perhalogeno-sulfonyl-imides, recourse is advantageously had to the process which consists of reacting the anhydride of the formula:

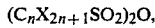

in which X and n have the above-indicated meanings, with the corresponding acid and urea, preferably in the absence of solvent, the mixture then being collected in an aqueous solution. The latter is then treated with a tetraalkylammonium halide, particularly tetrabutylammonium bromide, to precipitate the corresponding tetraalkylammonium bis-perhalogeno-sulfonyl-imide. By ionic exchange reaction, between the previously obtained compound and a reagent constituted by an alkali metal derivative, the compound according to the invention is finally obtained. The ionic exchange may be carried out particularly by bringing into play the differential solubilities in a system of solvents immiscible with one another, as will be illustrated in the embodiments formulated below, of the bis-perhalogeno-sulfonyl-imide of the alkali metal on the one hand, and of the derivative resulting from the substitution in the above said reagent of the alkali metal by the above said alkali-ammonium group on the other hand.

The ionic compounds according to the invention have quite satisfactory mutual dissolution qualities with poly(propylene oxide) and even, for compounds in which the R groups are constituted by hydrocarbon chains of short length, with poly(ethylene oxide). The solid solutions obtained have a cationic conductivity enabling their use as electrolyte materials for electrochemical generators, preferably of the rechargeable type, whose preferred characteristics are recalled below.

It relates therefore to the novel materials with ionic conduction, particularly cationic which are thus obtained, mor particularly a novel polymeric solid electrolyte constituted at least in part by a solid solution of one or several of the ionic compounds according to the invention, entirely dissolved within a macro-molecular material formed at least in part by a polymer, whose monomer units (of one or several types) include at least one hetero-atom, particularly oxygen or nitrogen, adapted to form bonds of the donor acceptor type with the cation of the ionic compound.

Preferably, the ratio of the number of hetero-atoms derived from the one or more monomeric units of said polymer to the number of atoms of the alkali metal of said ionic compound is comprised between 4 and 30, particularly 4 and 16. It is self-evident that the proportion of the ionic compound dissolved must be compatible with its solubility level in the selected polymer.

The alkali metal is preferably lithium or sodium.

The preferred plastic materials in which the ionic compounds according to the invention are placed in solution, are homo and/or copolymers derived from monometric units represented:

either by the following formula

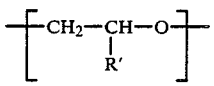

in which R' represents a hydrogen atom or one of the group Ra, —CH$_2$—O—Ra, —CH$_2$—O—Re—Ra, —CH$_2$—N=(CH$_3$)$_2$, with Ra representing an alkyl or a cycloalkyl radical including particularly 1 to 16, preferably 1 to 5 carbon atoms, Re representing a polyether radical of the general formula —(CH$_2$—CH$_2$—O)$_p$—, p having a value of 1 to 100, particularly from 1 to 2, or by the following formula:

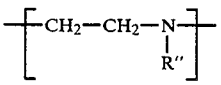

in which R" represents Ra, —Re—Ra, with Ra and Re having respectively one of the above-indicated meanings, or by the following formula:

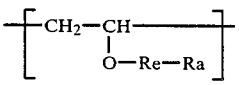

in which Ra and Re have respectively one of the above indicated meanings, or by the formula:

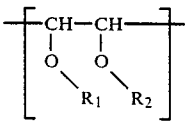

in which R$_1$ and R$_2$ are identical or different and each represent one of the groups Re, Re—Ra with the above meanings, and Re can then represent also a poly-ether of the formula

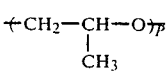

The preparation of the polymeric solid electrolyte may be carried out by the dissolving, in a solvent such as acetonitrile, or again methanol, of the polymer and of the ionic compound, then removal of the solvent, it being understood that a proporation of ionic compound is used less than that for which the solubility threshold is reached.

It is also possible to use any known method not restorting to solvent, for example by dissolving in the molten polymer.

The solid electrolytes produced according to the invention, find particularly advantageous application for the production of both primary and secondary electrochemical generators.

In particular, a solid electrolyte comprising in solution an ionic compound of the above-indicated type, may be associated with a negative electrode, constituted by a material adapted to provide the alkali ion corresponding to the metal of the ionic compound selected and a positive electrode adapted to incorporate the atoms of this metal. It is possible, for example, to provide a negative electrode constituted by the same alkali metal in the form of an alloy, or constituted by an intermetallic compound, an insertion compound or the like. For the positive electrode, it is possible to use any material whose crystalline structure enables the insertion of alkali metals. For example may be mentioned the chalcogenides which permit the diffusion of the alkali metal into their structure. It is possible again, as regard other examples of suitable materials for the formation of the positive electrodes, to refer to the already mentioned European patent application.

It is also possible to produce one of the electrodes, for example the positive one, by forming a composite from the active material of the latter and from these solid solution of the ionic compound, within the same macromolecular material. This composite can also include a compound inert to electronic conduction. It is also possible to resort, to constitute such electrodes and apart from the choice of the cationic compound, to the same methods of constitution as those described in European patent application No. 0013 199.

When these generators are constructed, it is observed that the novel electrolyte according to the invention has the advantage that the anion of the salt or ionic compound in solution is inert with respect to the majority of electrode materials that it is possible to use. This property enables a large number of cycles and stable storage. In addition, this chemical inertness confers on the generators which are thus constructed a very good resistance to thermal shock.

Other characteristics and advantages of the polymeric solid electrolytes according to the invention will appear in the embodiments which follow it being understood that these examples are in no way limiting.

These examples are indicative, particularly of the chemical and/or physical properties of particular ionic compounds of the invention and, in relationship with certain plastic electrolytes constituted with certain of some of them are indicative of the values of temperatures in °C. for which the conductivities are equal to about $10^{-5}\Omega^{-1}cm^{-1}(T\sigma 10^{-5})$, even to
$10^{-4}\Omega^{-1}cm^{-1}(T\sigma 10^{-4})$.

These measurements have been carried out in vacuum, so as to remove any trace of moisture and/or of solvent.

In all these examples, the macromolecular material is, as the case may be, a poly-(ethylene oxide) (POE) or a poly-(propylene oxide) of molecular weights equal or higher than 900,000. The electrolyte has been obtained by dissolving 1 g of this poly-(ethylene oxide) or this poly-(propylene oxide) in 35 ml of acetonitrile, then the addition of the ionic compound, to obtain atomic ratios O/Li or O/Na which are indicated below.

The solution so obtained is cast on a polytetrafluoroethylene support, to a thickness of 5 mm, then stoved at 60° C. for 3 hours.

The conductivity measurements were done by the techniques described by E. SCHOULER et al, J. Chim. Phys. 9 1309/16 (1973) and D. RAVAINE et al, J. Chim. Phys. 5 (93-70 (1974).

(1) Preparation of Bis(trifluoromethyl acetyl)imides

The reaction which is used to prepare this derivative compound is:

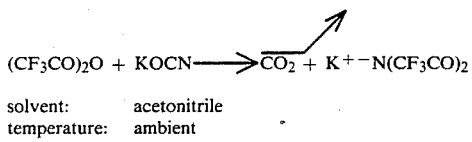

$(CF_3CO)_2O + KOCN \longrightarrow CO_2 + K^+{-}N(CF_3CO)_2$ solvent: acetonitrile
temperature: ambient The conversion of the potassium salt into a lithium salt is done by ionic exchange with LiCl, within an aqueous solution.

This compound has been characterised by its IR spectrum. It is represented in FIG. 1: variation of the transmission as a function, either of the wavelength, in microns, or of the wave number, in $cm^{-1}$. In the region 800-600 $cm^{-1}$ an impurity or may be a KOCN residue (marked as K. N. in the Figure) is observed.

(2) Preparation of Bis(trifluoromethyl sulfonyl)imides

Two reactions enable the desired compound $(CF_3SO_2)_2N$ to be obtained.

<u>1st reaction</u>

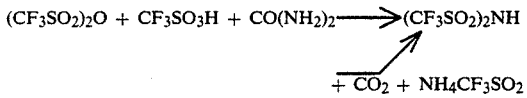

$(CF_3SO_2)_2O + CF_3SO_3H + CO(NH_2)_2 \longrightarrow (CF_3SO_2)_2NH$
$+ CO_2 + NH_4CF_3SO_2$ no solvent
ambient temperature.

The two products obtained after the reaction are then dissolved in water; the addition of tetrabutylammonium bromide to this solution enables the compound $(Bu)_4N^+{-}N(CF_3SO_2)_2$ to be precipitated.

2nd reaction $NH_4Cl + 2(CF_3SO_2)_2O + 4C_5H_5N \longrightarrow$ $C_5H_5NH^+{-}N(CF_3SO_2)_2 + C_5H_5NHCl + 2C_5H_5NHCF_3SO_3$ solvent: dichloromethane
temperature: ambient.

After removal of the solvent ($CH_2Cl_2$), the products of the reaction are dissolved in water. Tetrabutylammonium bromide added to this solution results in the precipitation of $(Bu)_4N^+{-}N(CF_3SO_2)_2$.

The corresponding sodium salt is obtained by the following ion exchange:

$(Bu)_4NN(CF_3SO_2)_2 + NaB(C_6H_5)_4 +{-}$
$(Bu)_4NB(C_6H_5)_4$ solvents: $H_2O$ and $CH_2Cl_2$.

The hydrophilic character of the $Na^+$ and $(CF_3SO_2)_2N^-$ ion enables migration in the aqueous phase. On the other hand, the hydrophilic ions $(Bu)_4N^+$ and $B(C_6H_5)_4^-$ are removed by the organic solution ($CH_2Cl_2$).

Figure 2:
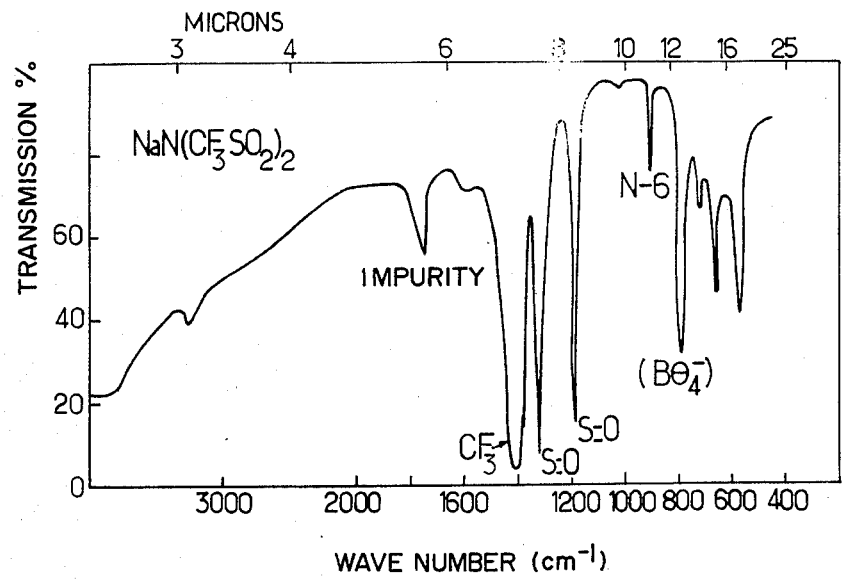
FIG. 2 is an IR spectrum of the compound sodium bis(trifluoromethyl-sulfonyl) imide.

FIG. 2 provides an IR spectrum of sodium bis(trifluoromethylsulfonyl)imide. The absorption peaks in the 800 $cm^{-1}$ region appear due to a trace of $B(C_6H_5)_4^-$.

In the table which follows the electrochemical data are provided obtained with the foregoing compounds, after dissolving in a POE, in relative atomic proportions which are also to be seen from the table.

| Ionic compound | Macromolecular material | O/M | $t\sigma\ 10^{-4}$ | $t\sigma\ 10^{-5}$ |
|---|---|---|---|---|
| $K^+N(CF_3CO_2)^-$ | POE | 12 | 44 | 42.2 |
| $Li^+N(CF_3CO_2)^-$ | POE | 8 | 73.5 | 46.75 |
| $Li^+N(CF_3CO_2)^-$ | POE | 12 | 64.8 | 47.5 |
| $Na^+N(CF_3SO_2)^-$ | POE | 12 | 60.7 | 45.6 |

These results testify as to the quite satisfactory conductivity of the solid solutions obtained, which may with advantage be used for the manufacture of electrochemical generators of the above-defined type.

We claim:

1. Ionic compound characterized by the formula:

$(C_nX_{2n+1}Y)_2N^-, M^+$ in which:
X is a halogen,
n varies from 1 to 4,
Y is a CO or $SO_2$ group and
M is a alkali metal.

2. Ionic compound according to claim 1, wherein X is fluorine.

3. Ionic compound according to claim 1, consisting of a bis(trifluoromethyl-acetyl)imide of an alkali metal.

4. Ionic compound according to claim 1, consisting of a bis(trifluoromethyl-sulfonyl)imide of an alkali metal.

5. Ionic compound according to claim 1, wherein M is constituted by lithium or sodium.

6. Ionic compound according to claim 1, characterized in that M is constituted by potassium.

7. Material with ionic conduction, constituted at least in part by a solid solution of one or several ionic compounds according to anyone of claims 1, 2, 3, 4, 5 or 6, entirely dissolved within a macromolecular material formed at least in part by a polymer whose monomer units include at least one hetero-atom, adapted to form bonds of the donor-acceptor type with a cation of the ionic compound.

8. Material with ionic conduction, according to claim 7, wherein the hetero-atom is oxygen or nitrogen.

9. Material with ionic conduction, constituted at least in part by a solid solution of one or several ionic compounds according to anyone of claims 1, 2, 3, 4, 5 or 6, entirely dissolved within poly(ethylene oxide) or poly(-propylene oxide).

10. Material with ionic conduction according to claim 7, wherein the ratio of the number of hetero-atoms derived from the monomer units of said macromolecular material to the number of atoms of alkali metal of said ionic compound is comprised between 4 and 30.

11. Material with ionic conduction according to claim 7, wherein the ratio of the number of hetero-atoms derived from the monomer units of said macromolecular material to the number of atoms of alkali metal of said ionic compound is comprised between 4 and 16.

12. Material with ionic conduction according to claim 9, wherein the ratio of the number of hetero-atoms derived from the monomer units of poly(ethylene oxide) or poly(propylene oxide) to the number of atoms of alkali metal of said ionic compound is comprised between 4 and 30.

13. Material with ionic conduction according to claim 9, wherein the ratio of the number of hetero-atoms derived from the monomer units of poly(ethylene oxide) or poly(propylene oxide) to the number of atoms of alkali metal of said ionic compound is comprised between 4 and 16.

14. Electrochemical generator, wherein its electrolyte is constituted by the material according to claim 7 and the negative electrode associated with it is constituted by a material adapted to supply the alkali ion corresponding to the metal of the selected ionic compound, and the positive electrode which is associated with it is adapted to incorporate the atoms of this metal.

15. Electrochemical generator, wherein its electrolyte is constituted by the material according to claim 9, and the negative electrode associated with it is constituted by a material adapted to supply the alkali ion corresponding to the metal of the selected ionic compound, and the positive electrode which is associated with it is adapted to incorporate the atoms of this metal.

16. An electrode structure which comprises a solid solution of an ionic compound according to claim 1 dissolved within a macromolecular material formed at least in part by a polymer whose monomer units include at least one hetero-atom, adapted to form bonds of the donor-acceptor type with a cation of the ionic compound.

17. The electrode structure of claim 16 wherein said electrode structure is a positive electrode and said structure includes alkali metals.

18. The electrode structure of claim 16 wherein said electrode structure is a negative electrode and said structure includes a material adapted to supply the alkali ion corresponding to the metal of the selected ionic compound.

* * * * *